United States Patent [19]

Hunsucker et al.

[11] 4,128,655
[45] Dec. 5, 1978

[54] IMIDAZOLINE COMPOUNDS USEFUL AS BACTERICIDES AND FUNGICIDES

[75] Inventors: Jerry H. Hunsucker; James R. Selleck, Jr., both of Terre Haute, Ind.

[73] Assignee: International Minerals & Chemical Corp., Terre Haute, Ind.

[21] Appl. No.: 776,801

[22] Filed: Mar. 11, 1977

[51] Int. Cl.$^2$ .............................................. A01N 9/22
[52] U.S. Cl. ............................................... 424/273 R
[58] Field of Search ......................... 424/273; 548/347

[56] References Cited

U.S. PATENT DOCUMENTS

| | | | |
|---|---|---|---|
| 2,392,326 | 1/1946 | Kyrides | 548/347 |
| 2,576,306 | 11/1951 | Morey | 548/300 |
| 3,290,328 | 12/1966 | Kollonitsch | 424/273 |
| 3,408,361 | 10/1968 | Manheimer | 548/347 |
| 3,502,578 | 3/1970 | Raifsnider | 548/347 |

FOREIGN PATENT DOCUMENTS

| | | | |
|---|---|---|---|
| 42-6839 | 3/1967 | Japan | 424/273 |
| 42-10382 | 5/1967 | Japan | 424/273 |

OTHER PUBLICATIONS

J.A.C.S., 70, 1629–1632 (1948) – J. L. Riebsomer.

Primary Examiner—Albert T. Meyers
Assistant Examiner—D. W. Robinson
Attorney, Agent, or Firm—Robert H. Dewey; Howard E. Post

[57] ABSTRACT

A method of controlling the growth of microorganisms by applying to them or to their habitat an imidazoline represented by the formula

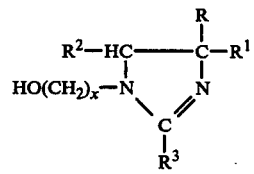

where R can be hydrogen or methyl, $R^1$ can be hydrogen, or alkyl of 1–3 carbon atoms, $R^2$ can be hydrogen or methyl, $R^3$ can be alkyl of 6–10 carbon atoms and $x$ is 1 or 2.

11 Claims, No Drawings

IMIDAZOLINE COMPOUNDS USEFUL AS BACTERICIDES AND FUNGICIDES

BACKGROUND OF THE INVENTION

This invention relates to a method of controlling the growth of microorganisms. In a particular aspect, this invention relates to a method of controlling the growth of microorganisms by the use of a member of the class of non-halogen substituted imidazolines.

One of the problems in metal working industries is the susceptibility of metalworking fluids (which are emulsions of oil in water, chemical lubricants in water, or mixtures of both) to microbial attack. Were it not for this microbial contamination, the fluids could be used for many months, but actually the microbial growth shortens the working life of the oil considerably. Microbial action may cause the emulsion to break and become acidic, thus causing corrosion problems. Some of the microbes may be pathogenic which can cause skin infections and other industrial health problems. In addition the microbial mycelia can clog pumps and valves, and often a foul odor develops. In a large installation, frequent replacement of metalworking fluids is costly.

SUMMARY OF THE INVENTION

It is an object of this invention to provide a method of controlling the growth of microorganisms.

It is another object of this invention to provide a method of controlling the growth of microorganisms using a substituted imidazoline.

Other objects of this invention will be apparent to those skilled in the art from the disclosure herein.

It is the discovery of this invention to provide a method of controlling the growth of microorganisms by applying to them or to their habitat an imidazoline represented by the formula $$\begin{array}{c} R \\ | \\ R^2-HC\underline{\quad\quad} C-R^1 \\ | \quad\quad\quad | \\ HO(CH_2)_x-N \quad\quad N \\ \diagdown \quad \diagup \\ C \\ | \\ R^3 \end{array}$$

where R can be hydrogen or methyl, $R^1$ can be hydrogen, or alkyl of 1–3 carbon atoms, $R^2$ can be hydrogen or methyl, $R^3$ can be alkyl of 6–10 carbon atoms and $x$ is 1 or 2.

DETAILED DISCUSSION

The compounds used in the practice of this invention are known in the art. They are prepared by condensing a primary diamine with a monocarboxylic aliphatic acid to form the imidazoline, then condensing the latter with formaldehyde or acetaldehyde. Methods for their preparation have been described by Morey, U.S. Pat. No. 2,576,306 and Riebsomer, J. Am. Chem. Soc. 70, 1629–32 (1948) and J. Org. Chem. 15, 68–73, 237–40, 241–4, 909–17 (1950).

The imidazolines preferred for the practice of this invention include but are not limited to:

$N^1$-hydroxymethyl-4-methyl-2-octyl-2-imidazoline
$N^1$-hydroxymethyl-4,4-dimethyl-2-octyl-2-imidazoline
$N^1$-hydroxymethyl-2-octyl-2-imidazoline
$N^1$-hydroxymethyl-2-hexyl-4-methyl-2-imidazoline
$N^1$-hydroxymethyl-2-decyl-4-methyl-2-imidazoline
$N^1$-hydroxymethyl-4-ethyl-2-octyl-2-imidazoline
$N^1$-hydroxymethyl-3,4-dimethyl-2-hexyl-2-imidazoline
$N^1$-hydroxymethyl-2-decyl-4-propyl-2-imidazoline
$N^1$-hydroxyethyl-4-methyl-2-octyl-2-imidazoline.

The compounds useful in the practice of this invention are generally effective to control the growth of bacteria or fungi at low concentrations, e.g. 100 ppm. There is of course no upper limit to the amount that can be used but generally they become uneconomical above about 5000 ppm and accordingly a use concentration of 100–5000 ppm is contemplated. Generally, however, a concentration between 100 and 2000 ppm is preferred and a concentration of 500–1000 ppm is particularly preferred.

The imidazolines are conveniently applied to the environment inhabited by microorganisms as an aqueous solution or dispersion. They are particularly effective in aqueous systems such as latex paints, starch adhesives and solutions, drilling muds for the petroleum industry, slurries of various types, in water-dilutable metalworking fluids based on petroleum hydrocarbons and in water treatment.

These imidazolines are also soluble in, e.g. alcohols, ketones and most other organic solvents, including hydrocarbons. Solutions of the water-insoluble imidazolines in such solvents can be used in substantially non-aqueous or 2-phase systems when desired.

The method of controlling the growth of microorganisms of this invention comprises application of the antimicrobial imidazolines of this invention to a substratum infested with the microorganisms to be controlled or to a substratum to be protected from infestation with the microorganisms. The terms microbe and microorganism as used herein are intended to include bacteria and fungi. The term antimicrobial as used herein is intended to include the terms bactericidal, bacteriostatic, fungicidal and fungistatic. No attempt has been made to determine if the products actually cause the death of the organism or merely prevent their growth.

The antimicrobial imidazolines of this invention are preferably supplied to the microorganisms or to their environment in the form of emulsions or suspensions. Emulsions or suspensions are prepared by dispersing one or more of the imidazolines of this invention in water with the aid of a surface active agent. The antimicrobial imidazolines can be emulsified directly or they can first be dissolved in an organic solvent and then emulsified. The term "surface active agent" includes the various "emulsifying agents," "dispersing agents," "wetting agents" and "spreading agents" that can be mixed with the imidazolines of this invention in order to obtain a dispersion of the imidazolines in water. These surface active agents include the well-known anionic, cationic, or non-ionic surface active agents. In general, the water-soluble non-ionic surface active agents are preferred.

In controlling the growth of microorganisms the imidazolines of this invention are supplied to the organisms or to their environment in a lethal or toxic amount. This can be done by dispersing one or more of the imidazolines in, on, or over an environment or substratum infested with, or to be protected form, the microorganisms. The imidazoline can be dispersed in any conventional method which permits contact between the organisms and the antimicrobial agents of this invention.

The invention will be better understood with reference to the following examples. The examples are intended only to illustrate the invention and it is not intended that the invention be limited thereby.

EXAMPLE 1

1,2-Diaminopropane 61.5 g (0.7 mole) was delivered to a reaction vessel and pelargonic acid 112 g (0.7 mole) was added slowly. The mixture was slowly heated to 170° C. while removing water of reaction. There was obtained 4-methyl-2-octyl-2-imidazoline. To it was added 42 g of paraformaldehyde with stirring. The mixture was heated to about 100° C. for 3 hours to produce $N^1$-hydroxymethyl-4-methyl-2-octyl-2-imidazoline.

The compound was tested for antimicrobial activity by determining the minimum inhibitory concentration (MIC) as is known in the art. The MIC is actually a range. The lower value is the highest concentration tested which permits growth and the higher value is the lowest concentration tested which prevents growth of the organism. The results obtained against 9 bacteria and 8 fungi are given in the following table.

| Minimum Inhibitory Concentrations, ppm | |
|---|---|
| Organism | |
| BACTERIA | |
| *Bacillus subtilis* | <32.25 |
| *Staphylococcus aureus* | <32.25 |
| *Streptococcus faecalis* | <32.25 |
| *Sarcina lutea* | <32.25 |
| *Escherichia coli* | 500–1000 |
| *Aerobacter aerogenes* | <32.25 |
| *Pseudomonas aeruginosa* | >2000 |
| *Salmonella typhi* | 1000–2000 |
| *Desulfovibrio aestuarii* | 64.5–125 |
| FUNGI | |
| *Cladosporium herbarum* | <32.25 |
| *Cephalosporium species* | <32.25 |
| *Trichophyton mentagrophytes* | 64.5–125 |
| *Aspergillus niger* | 250–500 |
| *Aureobasidium pullulans* | 125–250 |
| *Fusarium moniliforme* | 250–500 |
| *Saccharomyces cerevisiae* | 32.25–64.5 |
| *Candida albicans* | 125–250 |

A cutting oil emulsion is prepared according to the following formula:

| Light mineral oil | 20 | parts |
|---|---|---|
| Water | 76.5 | |
| Imidazoline prepared above | 0.5 | |
| Emulsifying agent | 3 | |
| | Total 100.0 | |

The emulsion remains free from microbial contamination for a prolonged period when used as a cutting oil.

EXAMPLE 2

The experiment of example 1 is repeated in all essential details except that 2-methyl-1,2-propanediamine is substituted for 1,2-diaminopropane on an equimolar basis. The resulting compound, $N^1$-hydroxymethyl-4,4-dimethyl-2-octyl-2-imidazoline, exhibits powerful antimicrobial activity.

EXAMPLE 3

The experiment of example 1 is repeated in all essential details except that 1,2-ethylenediamine is substituted for 1,2-diaminopropane on an equimolar basis. The resulting compound, $N^1$-hydroxymethyl-4,4-dimethyl-2-octyl-2-imidazoline, exhibits powerful antimicrobial activity.

EXAMPLE 4

The experiment of example 1 is repeated in all essential details except that caprillic acid is substituted for pelargonic acid on an equimolar basis. The resulting compound, $N^1$-hydroxymethyl-2-hexyl-4-methyl-2-imidazoline, exhibits powerful antimicrobial activity.

EXAMPLE 5

The experiment of example 1 is repeated in all essential details except that undecanoic acid is substituted for pelargonic acid on an equimolar basis. The resulting compound, $N^1$-hydroxymethyl-2-decyl-4-methyl-2-imidazoline, exhibits powerful antimicrobial activity.

EXAMPLE 6

The experiment of example 1 is repeated in all essential details except that 1,2-diaminobutane is substituted for 1,2-diaminopropane on an equimolar basis. The resulting compound, $N^1$-hydroxymethyl-4-ethyl-2-octyl-2-imidazoline, exhibits powerful antimicrobial activity.

EXAMPLE 7

The experiment of example 1 is repeated in all essential details except that 2,3-diaminobutane is substituted for 1,2-diaminopropane on an equimolar basis. The resulting compound, $N^1$-hydroxymethyl-3,4-dimethyl-2-octyl-2-imidazoline, exhibits powerful antimicrobial activity.

EXAMPLE 8

The experiment of example 1 is repeated in all essential details except that 1,2-diaminopentane is substituted for 1,2-diaminopropane. The resulting compound, $N^1$-hydroxymethyl-4-methyl-2-octyl-2-imidazoline, exhibits powerful antimicrobial activity.

EXAMPLE 9

The experiment of example 1 is repeated in all essential details except that acetaldehyde is substituted for paraformaldehyde on an equimolar basis. The resulting compound, $N^1$-hydroxyethyl-4-methyl-2-octyl-2-imidazoline, exhibits powerful antimicrobial activity.

We claim:

1. A method of controlling the growth of bacteria and fungi by applying to them or to the environment inhabited by them, a growth inhibiting amount of an imidazoline of the formula $$\begin{array}{c} R \\ | \\ R^2-HC\text{———}C-R^1 \\ | \quad\quad\quad | \\ HO(CH_2)_x-N \quad\quad N \\ \diagdown \;\; C \;\; \diagup \\ | \\ R^3 \end{array}$$

where R is hydrogen or methyl, $R^1$ is hydrogen or alkyl of 1–3 carbon atoms, $R^2$ is hydrogen or methyl, $R^3$ is alkyl of 6–10 carbon atoms and $x$ is 1 or 2.

2. The method of claim 1 wherein R and $R^1$ are methyl.

3. The method of claim 1 wherein R, $R^1$ and $R^2$ are hydrogen.

4. The method of claim 1 wherein R is hydrogen and $R^1$ is methyl, ethyl or propyl.

5. The method of claim 1 wherein $R^2$ is methyl.

6. The method of claim 1 wherein $x$ is 1.

7. The method of claim 1 wherein $x$ is 2.

8. The method of claim 1 wherein $R^3$ is methyl.

9. The method of claim 1 wherein $R^3$ is an alkyl group of 6 carbon atoms.

10. The method of claim 1 wherein $R^3$ is an alkyl group of 8 carbon atoms.

11. The method of claim 1 wherein $R^3$ is an alkyl group of 10 carbon atoms.

* * * * *

UNITED STATES PATENT AND TRADEMARK OFFICE
CERTIFICATE OF CORRECTION

PATENT NO. : 4,128,655
DATED : December 5, 1978
INVENTOR(S) : Jerry H. Hunsucker and James R. Selleck, Jr.

It is certified that error appears in the above-identified patent and that said Letters Patent are hereby corrected as shown below:

Column 2, line 65, "form" should read -- from --

*Signed and Sealed this*

*Twenty-second* Day of *May 1979*

[SEAL]

Attest:

RUTH C. MASON
*Attesting Officer*

DONALD W. BANNER
*Commissioner of Patents and Trademarks*